US011793740B2

(12) United States Patent
Griffiths et al.

(10) Patent No.: US 11,793,740 B2
(45) Date of Patent: Oct. 24, 2023

(54) HIGH-CONCENTRATE FLOWABLE LIQUID ANIONIC SURFACTANT COMPOSITION

(71) Applicant: ARXADA AG, Visp (CH)

(72) Inventors: Adam Stephen Griffiths, Blackley (GB); Jordan Todorov Petkov, Chesire (GB)

(73) Assignee: ARXADA AG, Visp (CH)

( * ) Notice: Subject to any disclaimer, the term of this patent is extended or adjusted under 35 U.S.C. 154(b) by 278 days.

(21) Appl. No.: 16/551,003

(22) Filed: Aug. 26, 2019

(65) Prior Publication Data

US 2020/0060951 A1 Feb. 27, 2020

Related U.S. Application Data

(60) Provisional application No. 62/723,275, filed on Aug. 27, 2018.

(51) Int. Cl.
| | |
|---|---|
| *A61K 8/00* | (2006.01) |
| *A61K 8/46* | (2006.01) |
| *A61Q 5/02* | (2006.01) |
| *A61K 8/37* | (2006.01) |
| *A61K 8/34* | (2006.01) |
| *A61Q 19/10* | (2006.01) |

(52) U.S. Cl.
CPC .............. *A61K 8/463* (2013.01); *A61K 8/345* (2013.01); *A61K 8/347* (2013.01); *A61K 8/375* (2013.01); *A61Q 5/02* (2013.01); *A61Q 19/10* (2013.01)

(58) Field of Classification Search
CPC ...................................................... A61K 8/463
See application file for complete search history.

(56) References Cited

U.S. PATENT DOCUMENTS

| | | | |
|---|---|---|---|
| 6,313,085 B1 | 11/2001 | Le Hen-Ferrenbach | |
| 10,517,807 B2 * | 12/2019 | Lipinski | A61Q 5/12 |
| 2013/0053295 A1 * | 2/2013 | Kinoshita | C11D 1/02 |
| | | | 510/427 |
| 2014/0290687 A1 * | 10/2014 | Takiguchi | A61K 8/463 |
| | | | 132/202 |

FOREIGN PATENT DOCUMENTS

| | | |
|---|---|---|
| EP | 1696023 | 8/2006 |
| WO | WO9325650 | 12/1993 |
| WO | WO9909944 | 3/1999 |

OTHER PUBLICATIONS

International Search Report for PCT/IB2019/057211 dated Dec. 12, 2019, 6 pages.

* cited by examiner

*Primary Examiner* — Necholus Ogden, Jr.
(74) *Attorney, Agent, or Firm* — Dority & Manning, P.A.

(57) ABSTRACT

Described is a high-concentrate flowable liquid anionic surfactant composition containing an alkyl ether sulfate and a viscosity modifier(s). The composition avoids the highly viscous gel phase that occurs when concentrated anionic surfactants are diluted with an aqueous solvent. Also described, is a personal care composition of the high-concentrate flowable liquid anionic surfactant composition.

23 Claims, 9 Drawing Sheets

HIGH-CONCENTRATE FLOWABLE LIQUID ANIONIC SURFACTANT COMPOSITION

FIELD OF INVENTION

The disclosure relates to a high-concentrate flowable liquid anionic surfactant composition which remains flowable when diluted with an aqueous solvent; and a method of reducing the viscosity increase of a high-concentrate liquid anionic surfactant composition when diluted with an aqueous solvent.

BACKGROUND OF THE INVENTION

Concentrated forms of anionic surfactants, such as 70% sodium lauryl ether sulfate (SLES), upon dilution to as low as 30% concentration forms a highly viscoelastic gel (cubic) phase. When this gel phase occurs, SLES is difficult to pump using conventional pumps and specialized equipment is required, making the process timely and very expensive. When gelling occurs, the formation makes cleaning of pipes, reaction vessels, transportation vessels and the like difficult; more importantly, gelation slows down the dissolution rate of products in water at the time of application.

Additionally, such concentrated/diluted forms of SLES can exhibit instability when unexpectedly heated above approximately 140° F. The product can hydrolyze, releasing sulfuric acid, thus damaging process equipment. The heat of a product process reaction, once it is started, does not dissipate because of the gel nature of high active SLES. This can lead to very high temperatures in the process reaction, and further lead to a runaway reaction, which can destroy the whole product batch.

To avoid unnecessary mass transport, it is an advantage if water-containing surfactant gels or pastes have a high solid content. However, alkyl sulfate gels or pastes can only be concentrated to a certain solid content. In addition, such gels and pastes show non-newtonian flow behavior.

One method for overcoming the high viscosity of high active surfactants, when diluted at varied concentrations, is through the addition of viscosity modifiers such as volatile solvents (such as iso-propanol); thinning agent such as propylene glycol and the like. However, such substances are flammable solvents, which results in added safety concerns during the preparation process, storage and/or shipping operations. Additionally, the use of such actives result in the thinning of SLES thereby affecting the use of such compositions in formulations as they cannot be further thickened, thereby compromising the processing of SLES in end-user formulations. Ultimately, there is still a need for a suitable viscosity modifier for anionic surfactants such as SLES at high concentrations.

The present disclosure provides an answer to that need by describing a high-concentrate flowable liquid anionic surfactant composition, which remains flowable, when diluted with an aqueous solvent. Furthermore, the present disclosure also discloses a method of overcoming the problem of very high or irreversibly low viscosities of certain anionic compositions, by providing a viscosity modifier such as an aromatic alcohol, polyglyceryl ester or alkyl glyceryl ether; which suppresses the cubic viscoelastic phase behavior of anionic surfactants such as SLES between 70%-30% concentrated. Moreover, in one aspect, the present disclosure has found that the method and high-concentrate flowable liquid anionic surfactant composition may additionally delay the onset of the gel phase.

The present disclosure has further found that, in one aspect, the composition and method may provide the above discussed benefits without the use of flammable solvents or thinning agent such as propylene glycol and the like. Furthermore, the method and composition may also provide the benefit of having multi-functional applications in personal care compositions. Particularly, in an aspect, the composition may function as a viscosity modifier and/or preservative, emulsifier, skin conditioning agent, deodorizer, stabilizing agent, and the like, thereby reducing the number of ingredients used in fluid formulations, and reducing cost, time, and energy.

The resulting anionic surfactant composition, once blended, is more stable, and when diluted at varied concentrations, remains completely flowable. Thus, the flowable composition containing the anionic surfactant may be easily pumped, transported or stored over a varied temperature range, thereby improving the processability of high activity SLES, even at large scale, in one aspect, without the need for special equipment. In yet a further aspect, the flowable composition does not separate upon storage or at varied temperatures. Therefore, in one aspect, compositions according to the present disclosure provide a clear, concentrated, liquid composition capable of being easily diluted or formulated, resulting in an improved ease of handling and pumping using non-specialized equipment, which may ultimately eliminate the use of flammable solvents; special equipment to prepare, store or transport cost, and space of such compositions.

Furthermore, in an aspect, the present disclosure describes a flowable composition comprising an anionic surfactant and viscosity modifier, that, when diluted with an aqueous solvent, remains flowable and has a viscosity value of less than 3,000 pascal seconds, at a shear rate of 0.25 s$^{-1}$ and at a temperature of 30° C. The use of specific viscosity modifiers suppresses the cubic viscoelastic phase behavior of anionic surfactants such as SLES between 70%-30% concentrated, and additionally delays the onset of the gel phase. The disclosure encompasses the knowledge that the preparations in particular also permit the stable and non-turbid incorporation of anionic surfactants, into personal care applications.

SUMMARY OF THE INVENTION

In one aspect, the present invention provides a high-concentrate flowable liquid anionic surfactant composition which remains flowable, when diluted with an aqueous solvent; and a method of reducing the viscosity increase of a high-concentrate liquid anionic surfactant composition, when diluted with an aqueous solvent.

In accordance with the present invention, describes a high-concentrate flowable liquid anionic surfactant composition comprising: (a) an anionic surfactant solution comprising 30 w/w % to 90 w/w % by weight of an alkyl ether sulfate, having a Formula (I):

$$R^1O(CH_2CH_2O)_nSO_3X \qquad (I)$$

wherein $R^1$ is a $C_8$-$C_{32}$ linear or branched, substituted or unsubstituted alkyl, n is a number having a value from 0.5-10, X is an alkali metal, alkaline earth metal, ammonium, alkylammonium, alkanolammonium or glucammonium;

(b) 0.01 w/w % to 20 w/w % of a viscosity modifier comprising an aromatic alcohol, a $C_6$-$C_{22}$ linear or branched polyglyceryl ester, alkyl glyceryl ether or combinations thereof; and (c) an aqueous solvent in an amount sufficient for the total of components equaling 100%; wherein upon dilution with an aqueous solvent, the composition remains flowable.

In one particular embodiment, the aqueous solvent is water.

In one embodiment, $R^1$ comprises a caprylic, capric, lauryl, isotridecyl, myristyl, cetyl, stearyl, oleyl, isostearyl, arachidyl, or behenyl, or mixtures thereof.

In a particular embodiment, the high-concentrate flowable liquid anionic surfactant composition, is one in which the alkyl ether sulfate, comprises a sodium lauryl ether sulfate, ammonium lauryl ether sulfate or combinations thereof.

In one embodiment, the viscosity modifier is an aromatic alcohol comprising benzyl alcohol, phenoxyethanol or derivatives thereof, or mixtures thereof.

In another embodiment, the viscosity modifier is a $C_6$-$C_{22}$ linear or branched polyglyceryl ester comprising polyglyceryl-10 caprylate/caprate.

In yet another embodiment, the viscosity modifier is an alkyl glyceryl ether comprising ethylhexylglycerin.

In one embodiment, X comprises an alkali metal comprising sodium or potassium; an alkaline earth metal comprising magnesium or calcium; alkylammonium, alkanolammonium or glucammonium.

In one embodiment, n is a value from 0.5 to 5.

In one particular embodiment, the high-concentrate flowable liquid anionic surfactant composition comprises of 40 w/w % to 75 w/w % active of an alkyl ether sulfate.

In one embodiment, diluted high-concentrate flowable liquid anionic surfactant composition has a viscosity value less than 3,000 pascal seconds, at a shear rate of 0.25 s$^{-1}$ and at a temperature of 30° C., when diluted in an aqueous solvent In one particular embodiment, the high-concentrate flowable liquid anionic surfactant composition comprises: (a) 45 w/w % to 75 w/w % of an alkyl ether sulfate comprising sodium lauryl ether sulfate, ammonium lauryl ether sulfate or combinations thereof; and (b) 0.01 w/w % to 20 w/w % of viscosity modifier comprising phenoxyethanol, benzyl alcohol, 4-(2-Hydroxyethyl)phenol, ethylhexylglycerin, polyglyceryl-10 caprylate/caprate, or combinations thereof.

One particular embodiment, describes the method of reducing the viscosity increase of a high-concentrate liquid anionic surfactant when diluted with an aqueous solvent has a viscosity value of less than 3,000 pascal seconds, at a shear rate of 0.25 s$^{-1}$ and at a temperature of 30° C.

Another aspect of the invention provides a method of reducing the viscosity increase of a high-concentrate liquid anionic surfactant composition when diluted with an aqueous solvent.

One particular embodiment describes a method of reducing the viscosity increase of a high-concentrate liquid anionic surfactant composition during dilution with water, said method comprising:

(i) providing an anionic surfactant concentrate which exhibits a viscosity increase during dilution with an aqueous solvent,
(ii) adding a viscosity modifier into said anionic surfactant concentrate; and
(iii) mixing the viscosity modifier and the anionic surfactant concentrate together.

In one embodiment, the method as described, comprises: (a) an anionic surfactant containing 30 w/w % to 90 w/w % by weight of an alkyl ether sulfate, having a Formula (I):

$$R^1O(CH_2CH_2O)_nSO_3X \qquad (I)$$

wherein $R^1$ is a $C_8$-$C_{32}$ linear or branched, substituted or unsubstituted alkyl,
n is a number having a value from 0.5-10;
X is an alkali metal, alkaline earth metal, ammonium, alkylammonium, alkanolammonium or glucammonium; and
(ii) water in an amount sufficient for the total of components equal 100%.
(b) 0.01 w/w % to 20 w/w % of a viscosity modifier comprising an aromatic alcohol, a $C_6$-$C_{22}$ linear or branched polyglyceryl ester, alkyl glyceryl ether or combinations thereof; and
(c) an aqueous solvent in an amount sufficient for the total of components equal 100%; wherein upon dilution with the aqueous solvent, the composition remains flowable.

In one embodiment, the viscosity modifier comprises a blend of two or more viscosity modifier added together at various ratios from about 1:100 to 100:1.

In yet another aspect of the present invention, a personal care composition 0.01 w/w % to 50 w/w %, of the high-concentrate flowable liquid anionic surfactant composition, having a Formula (I) as previously described, based on the total weight of the personal care composition.

These and other aspects will become apparent when reading the detailed description of the invention.

DETAILED DESCRIPTION

The term "high-concentrate flowable liquid" refers to a concentrated anionic surfactant having a viscosity value is less than 3000 pascal seconds, at a shear rate of 0.25 s$^{-1}$ and at a temperature of about 30° C. The term "flowable" refers to a composition cable of flowing and not having a gel like consistency.

It has now been surprisingly found that a high-concentrate flowable liquid anionic surfactant composition can be achieved for alkyl ether sulfate surfactants by using viscosity modifiers, specifically aromatic alcohols, polyglyceryl esters, alky glyceryl ethers, or mixtures thereof, and the like. Such components have multi-functional applications within personal care compositions such as preservatives, emulsifiers, skin conditioning agent, deodorizer, stabilizing agent, as well as viscosity modifying agents.

The present disclosure encompasses a high-concentrate flowable liquid anionic surfactant composition, which remains flowable when diluted with an aqueous solvent; and a method of reducing the viscosity increase of a high-concentrate liquid anionic surfactant composition, and delaying the onset of the gel phase, when diluted with an aqueous solvent. The presence of a viscosity modifier suppresses the cubic viscoelastic phase behavior of the anionic surfactant and further delays the onset of the gel phase it may form over time.

The present disclosure also describes a method of reducing the viscosity increase of a high-concentrate liquid anionic surfactant composition, when diluted with an aqueous solvent. Using the method as described, the viscosity of such compositions is a value less than 3,000 pascal seconds, at a shear rate of 0.25 s$^{-1}$ and at a temperature of about 30° C., when diluted with an aqueous solvent.

Accordingly, a preferred embodiment describes a high-concentrate flowable liquid anionic surfactant composition comprising: (a) an anionic surfactant solution comprising 30 w/w % to 90 w/w % by weight of an alkyl ether sulfate, having a Formula (I):

$$R^1O(CH_2CH_2O)_nSO_3X \quad (I)$$

wherein R$^1$ is a C$_8$-C$_{32}$ linear or branched, substituted or unsubstituted alkyl, n is a number having a value from 0.5-10, X is an alkali metal, alkaline earth metal, ammonium, alkylammonium, alkanolammonium or glucammonium;

(b) 0.01 w/w % to 20 w/w % of a viscosity modifier comprising an aromatic alcohol, a C$_6$-C$_{22}$ linear or branched polyglyceryl ester, alkyl glyceryl ether or combinations thereof; and (c) an aqueous solvent in an amount sufficient for the total of components equaling 100%; wherein upon dilution with an aqueous solvent, the composition remains flowable.

Examples of aqueous solvent include, but is not limited to, water, aqueous alcohols, ammonia water, acid solutions, salt solutions, water-miscible organic solvents, glycols, or mixtures thereof, and the like. Suitably the aqueous solvent includes water.

Typically, X is an alkali metal including, but not limited to, sodium or potassium, and the like; an alkaline earth metals including, but not limited to, magnesium or calcium, and the like; an alkylammonium, alkanolammonium or glucammonium, and the like.

As illustrated in Formula (I), the alkyl ether sulfonate is typically based on a 0.5 to 10 mol ratio of ethylene oxide to a C$_8$-C$_{32}$ alcohol in the form of their alkaline metal, alkaline earth metal and/or alkanolamine salts; suitably in a 1-5 mol ratio; desirably in a 1-3 mol ratio; See FIGS. 8 and 9.

The R$^1$ is a C$_8$-C$_{32}$ alkyl group including, but not limited to, caprylic, capric, lauryl, isotridecyl, myristyl, cetyl, stearyl, oleyl, isostearyl, arachidyl, or behenyl, or mixtures thereof, and the like.

Suitably, R$^1$ comprises a caprylic, capric, lauryl, isotridecyl, myristyl, cetyl, stearyl, oleyl, isostearyl, arachidyl, or behenyl, or mixtures thereof, and the like. Desirably R$^1$ comprises a lauryl group.

For example, R$^1$ comprises a lauryl alkyl group, in which the alkyl ether sulfate, having a Formula (I), specifically sodium lauryl ether sulfate, ammonium lauryl ether sulfate, or combinations thereof, and the like.

Typically, the anionic surfactant solution comprising 30 w/w % to 90 w/w % of an alkyl ether sulfate, having a Formula (I); Suitably the solution comprises 40 w/w % to 80 w/w % active of an alkyl ether sulfate; or desirably the solution comprises 45 w/w % to 75 w/w % active of an alkyl ether sulfate as described above.

The viscosity modifier comprises an aromatic alcohol, a C$_6$-C$_{22}$ linear or branched polyglyceryl ester, alkyl glyceryl ether or combinations thereof, and the like.

Suitably, the viscosity modifier is present in a range from 0.01 w/w % to 20 w/w % of the total composition; desirably, the viscosity modifier may be present in a range from 0.01 w/w % to 10 w/w % of the total composition.

Examples of aromatic alcohols include, but are not limited to, benzyl alcohol, 4-methoxybenzyl alcohol, 4-methylbenzyl alcohol, 4-isopropyl-benzyl alcohol, 2-phenylethanol, dl-1-phenethylalcohol, phenoxyethanol or derivatives thereof (i.e. 4-(2-Hydroxyethyl)phenol), 1-phenyl-1-propanol, 2-methyl-1-phenyl-2-propanol, cinnamic alcohol, alpha-amylcinnamyl alcohol, 1-pentanol, 3-methyl-5-phenyl, 2-(4-methylphenyl) ethanol, or mixtures thereof, and the like.

Suitably, the aromatic alcohol includes phenoxyethanol, 4-(2-Hydroxyethyl)phenol, benzyl alcohol, or mixtures thereof.

Examples of alkyl glyceryl ethers include, but are not limited to, ethylhexylglycerin, glyceryl lauryl ether and isostearyl glyceryl ether, cetyl glyceryl ether, octadecyl glyceryl ether and the like. Suitably the alkyl glyceryl ether includes ethylhexylglycerin.

Typical examples of the C$_6$-C$_{22}$ linear or branched polyglyceryl esters include, but are not limited to, polyglyceryl monodecaoleate such as polyglyceryl-10 decaoleate; polyglyceryl monooleate such as polyglyceryl-2-monooleate, polyglyceryl-3 monooleate, polyglyceryl-4 monooleate, polyglyceryl-6 monooleate, or polyglyceryl-10 monooleate; polyglyceryl dioleate such as polyglyceryl-2 dioleate, polyglyceryl-3 dioleate, polyglyceryl-5 dioleate, polyglyceryl-6 dioleate or polyglyceryl-10 dioleate; polyglyceryl trioleate such as polyglyceryl-5 trioleate or polyglyceryl-10 trioleate; polyglyceryl tetraoleate such as polyglyceryl-2 tetraoleate, polyglyceryl-6 tetraoleate, or polyglyceryl-10 tetraoleate; polyglyceryl pentaoleate such as polyglyceryl-4 pentaoleate, polyglyceryl-6 pentaoleate, or polyglyceryl-10 pentaoleate; polyglyceryl heptaoleate such as polyglyceryl-6 heptaoleate, polyglyceryl-10 heptaoleate; polyglyceryl monostearate such as polyglyceryl-2 monostearate, polyglyceryl-3 monostearate, polyglyceryl-4 monostearate, polyglyceryl-5 monostearate, polyglyceryl-6 monostearate or polyglyceryl-10 monostearate; polyglyceryl distearate such as polyglyceryl-2 distearate, polyglyceryl-3 distearate, polyglyceryl-4 distearate, polyglyceryl-6 distearate, or polyglyceryl-10 distearate; polyglyceryl tristearate such as polyglyceryl-4 tristearate, polyglyceryl-5 tristearate, polyglyceryl-6 tristearate, or polyglyceryl-10 tristearate; polyglyceryl tetrastearate such as polyglyceryl-2 tetrastearate; polyglyceryl pentastearate such as polyglyceryl-4 pentastearate, polyglyceryl-6 pentastearate, or polyglyceryl-10 pentastearate; polyglyceryl heptastearate such as polyglyceryl-10 heptastearate; polyglyceryl isostearate such as polyglyceryl-2 isostearate, polyglyceryl-3 isostearate, polyglyceryl-4 isostearate, polyglyceryl-6 isostearate, or polyglyceryl-10 isostearate; polyglyceryl diisostearate such as polyglyceryl-2 diisostearate. polyglyceryl-3 diisostearate, polyglyceryl-4 diisostearate, polyglyceryl-6 diisostearate, polyglyceryl-10 diisostearate, or polyglyceryl-15 diisostearate; polyglyceryl triisostearate such as polyglyceryl-2 triisostearate, polyglyceryl-3 triisostearate, polyglyceryl-5 triisostearate, polyglyceryl-10 triisostearate; polyglyceryl tetraisostearate such as polyglyceryl-2 tetraisostearate; polyglyceryl caprylate such as polyglyceryl-2 caprylate, polyglyceryl-3 caprylate, polyglyceryl-4 caprylate, polyglyceryl-6 caprylate, or polyglyceryl-10 caprylate; polyglyceryl dicaprylate such as polyglyceryl-5 dicaprylate; polyglyceryl sesquicaprylate such as polyglyceryl-2 sesquicapyrlate; polyglyceryl octacaprylate such as polyglyceryl-6 octacaprylate; polyglyceryl caprate such as polyglyceryl-2 caprate, polyglyceryl-3 caprate, polyglyceryl-4 caprate, polyglyceryl-5 caprate, polyglyceryl-6 caprate, polyglyceryl-10 caprate: polyglyceryl dicaprate such as polyglyceryl-3 dicaprate or polyglyceryl-6 dicaprate; polyglyceryl caprylate/caprate such as polyglyceryl-4 capyrlateicaprate, polyglyceryl-6 caprylate/caprate, or polyglyceryl-10 caprylate/caprate; polyglyceryl palmitate such as polyglyceryl-2 palmitate, polyglyceryl-3 palmitate, polyglyceryl-6 palmitate or polyglyceryl-10 palmitate; polyglyceryl dipalmitate such as polyglyceryl-6 dipalmitate or polyglyceryl-10 dipalmitate; polyglyceryl tetrabehenate such as polyglyceryl-6 tetrabehenate; polyglyceryl myristate such as polyglyceryl-6 myristate or polyglyceryl-10 myristate; polyglyceryl rincinoleate such polyglyceryl-6 polyricinoleate or polyglyceryl-10 ricinoleate; other derivatives thereof, or mixtures thereof, and the like.

Suitable examples of the $C_6$-$C_{22}$ linear or branched polyglyceryl esters include, but are not limited to, polyglyceryl-4 caprylate/caprate, polyglyceryl-5 caprylate/caprate, polyglyceryl-6 caprylate/caprate, polyglyceryl-7 caprylate/caprate, polyglyceryl-8 caprylate/caprate, polyglyceryl-9 caprylate/caprate, polyglyceryl-10 caprylate/caprate, polyglyceryl-4 caprate, polyglyceryl-5 caprate, polyglyceryl-6 caprate, polyglyceryl-7 caprate, polyglyceryl-8 caprate, polyglyceryl-9 caprate, polyglyceryl-10 caprate, polyglyceryl-4 laurate, polyglyceryl-5 laurate, polyglyceryl-6 laurate, polyglyceryl-7 laurate, polyglyceryl-8 laurate, polyglyceryl-9 laurate, polyglyceryl-10 laurate, polyglyceryl-6 cocoate, polyglyceryl-7 cocoate, polyglyceryl-8 cocoate, polyglyceryl-9 cocoate, polyglyceryl-10 cocoate, polyglyceryl-11 cocoate, polyglyceryl-12 cocoate, polyglyceryl-6 myristate, polyglyceryl-7 myristate, polyglyceryl-8 myristate, polyglyceryl-9 myristate, polyglyceryl-10 myristate, polyglyceryl-11 myristate, polyglyceryl-12 myristate, polyglyceryl-10 oleate, polyglyceryl-11 oleate, polyglyceryl-12 oleate, polyglyceryl-10 decaoleate, polyglyceryl-3 stearate, polyglyceryl-6 distearate, polyglyceryl-10 stearate, polyglyceryl-10 dipalmitate, polyglyceryl-10 oleate, polyglyceryl-10 caprylate/caprate, polyglyceryl polyricinoleate, polyglyceryl-4 stearate, polyglyceryl-3 caprylate/caprate, polyglyceryl-6 stearate, polyglyceryl-10 laurate, polyglyceryl-10 cocoate, polyglyceryl-10 myristate, polyglyceryl-12 laurate, or combinations thereof, and the like.

Desirably, the polyglyceryl ester includes polyglyceryl-10 caprylate/caprate.

Suitably, the high-concentrate flowable liquid anionic surfactant composition, includes (a) 45 w/w % to 75 w/w % of an alkyl ether sulfate including sodium lauryl ether sulfate, ammonium lauryl ether sulfate or combinations thereof; and (b) 0.01 w/w % to 20 w/w % of viscosity modifier including phenoxyethanol, benzyl alcohol, 4-(2-Hydroxyethyl)phenol, ethylhexylglycerin, polyglyceryl-10 caprylate/caprate, or combinations thereof.

For example, the high-concentrate flowable liquid anionic surfactant composition includes (a) 45 w/w %-75 w/w % weight of an alkyl ether sulfate such as sodium lauryl ether sulfate, ammonium lauryl ether sulfate or combinations thereof; and (b) 0.01 w/w %-20 w/w % of aromatic alcohol, in which the aromatic alcohol may be a phenoxyethanol, benzyl alcohol or combinations thereof.

In another example, the high-concentrate flowable liquid anionic surfactant composition includes (a) 45 w/w % to 75 w/w % weight of an alkyl ether sulfate such as sodium lauryl ether sulfate, ammonium lauryl ether sulfate or combinations thereof; and (b) 0.01 w/w % to 20 w/w % of an aromatic alcohol, specifically phenoxyethanol.

In a further example, the high-concentrate flowable liquid anionic surfactant composition includes (a) 45 w/w % to 75 w/w % weight of an alkyl ether sulfate such as sodium lauryl ether sulfate, ammonium lauryl ether sulfate or combinations thereof; and (b) 0.01 w/w % to 20 w/w % of aromatic alcohol, specifically benzyl alcohol.

Alternately, the high-concentrate flowable liquid anionic surfactant composition includes (a) 45 w/w % to 75 w/w % weight of an alkyl ether sulfate such as sodium lauryl ether sulfate, ammonium lauryl ether sulfate or combinations thereof; and (b) 0.01 w/w % to 20 w/w % of aromatic alcohol, specifically ethylhexylglycerin.

Furthermore, the high-concentrate flowable liquid anionic surfactant composition includes (a) 45 w/w % to 75 w/w % weight of an alkyl ether sulfate such as sodium lauryl ether sulfate, ammonium lauryl ether sulfate or combinations thereof; and (b) 0.01 w/w % to 20 w/w % of a $C_6$-$C_{22}$ polyglyceryl ester, specifically polyglyceryl-10 caprylate/caprate.

Various high-concentrate flowable liquid anionic surfactant compositions can be formulated using a viscosity modifier as described above, or as a blend. The blend may contain two or more viscosity modifier added together at various ratios ranging typically from about 1:100 to 100:1; suitably 1:50 to 50:1 or desirably 1:25 to 25:1.

For example, as desired the viscosity modifier may include one or more of a phenoxyethanol, 4-(2-Hydroxyethyl)phenol, benzyl alcohol, ethylhexylglycerin, polyglyceryl-10 caprylate/caprate; wherein the viscosity modifiers are present in varied ratios ranging typically from about 1:100 to 100:1.

For example, in one embodiment, a high-concentrate flowable liquid anionic surfactant composition includes (a) 45 w/w % to 75 w/w % of an alkyl ether sulfate such as sodium lauryl ether sulfate, ammonium lauryl ether sulfate or combinations thereof; and a (b) 1:1 ratio of 0.01 w/w % to 10 w/w % phenoxyethanol and 0.01 w/w % to 10 w/w % polyglyceryl-10 caprylate/caprate.

In another example containing blends of viscosity modifiers, the high-concentrate flowable liquid anionic surfactant composition includes (a) 45 w/w % to 75 w/w % weight of an alkyl ether sulfate such as sodium lauryl ether sulfate, ammonium lauryl ether sulfate or combinations thereof; and (b) a mixture of 0.01 w/w % to 10 w/w % phenoxyethanol and 0.01 w/w % to 10 w/w % ethylhexylglycerin.

The addition of a viscosity modifier, as described above, results in a diluted anionic surfactant composition having a viscosity value less than 3,000 pascal seconds, at a shear rate of 0.25 s$^{-1}$ and at a temperature of about 30° C., when diluted in an aqueous solvent.

Another aspect of the present invention, describes a personal care composition containing from 0.01 w/w % to 50 w/w %, of the high-concentrate flowable liquid anionic surfactant composition as described, based on the total weight of the personal care composition. Personal care compositions may include, but not limited to hair-care and body-care products, cleansing products, cleaning products, cleansing products, or mixtures thereof, and the like.

Another aspect of the present invention, describes a method of reducing the viscosity increase of a high-concentrate liquid anionic surfactant composition during dilution with an aqueous solvent. Furthermore, in one aspect, a method of reducing the viscosity increase of a high-concentrate liquid anionic surfactant composition during dilution with water includes:
  (i) providing an anionic surfactant concentrate which exhibits a viscosity increase during dilution with an aqueous solvent,
  (ii) adding a viscosity modifier into said anionic surfactant concentrate; and
  (iii) mixing the viscosity modifier and the anionic surfactant concentrate together.

The embodiment of the method as described above and shown in FIG. 1-9, illustrates that the diluted anionic surfactant composition has a Rheometer viscosity value of less than 3,000 pascal seconds, at a shear rate of 0.25 s$^{-1}$, and at a temperature of about 30° C., when diluted with an aqueous solvent. The viscosity modifiers showed heavily suppressed peaks in comparison to the viscosity peaks of SLES alone.

According to the method as described, the anionic surfactant concentrate, includes: (a) an anionic surfactant comprising 30 w/w % to 90 w/w % of an alkyl ether sulfate, having a Formula (I):

$$R^1O(CH_2CH_2O)_nSO_3X \quad (I)$$

wherein R$^1$ is a C$_8$-C$_{32}$ linear or branched, substituted or unsubstituted alkyl, n is a number having a value from 0.5-10;

X is an alkali metal, alkaline earth metal, ammonium, alkylammonium, alkanolammonium or glucammonium;

(b) 0.01 w/w % to 20 w/w % of a viscosity modifier comprising an aromatic alcohol, a C$_6$-C$_{22}$ linear or branched polyglyceryl ester, alkyl glyceryl ether or combinations thereof; and (c) an aqueous solvent in an amount sufficient for the total of components equal 100%; wherein upon dilution with the aqueous solvent, the composition remains flowable.

Further descriptions for, R$^1$, X, n, viscosity modifiers, aqueous solvents are as previously described above. Furthermore, the method as described includes a blend of two or more viscosity modifiers having varied ratios ranging from about 1-100 to 100-1.

For example, the method as described comprises an alkyl ether sulfate, having a Formula (I) wherein the ether includes sodium lauryl ether sulfate, ammonium lauryl ether sulfate or combinations thereof.

The aromatic alcohol, as described in the method above, includes benzyl alcohol, phenoxyethanol, 4-(2-Hydroxyethyl)phenol, or combinations thereof.

Additionally, the C$_6$-C$_{22}$ linear or branched polyglyceryl ester, as described in the method above, includes polyglyceryl-10 caprylate/caprate.

Alternately, the alkyl glyceryl ether, as described in the method above, includes ethylhexylglycerin.

The aqueous solvent, as described in the method above, includes water.

One method describes the anionic surfactant concentrate, whereby the alkyl ether sulfate, having a Formula (I) includes a sodium lauryl ether sulfate, ammonium lauryl ether sulfate or combinations thereof; the viscosity modifier is added in an amount of 0.01 w/w % to 20 w/w %, based on the total weight of anionic surfactant concentrate, the viscosity modifier includes an aromatic alcohol, a C$_6$-C$_{22}$ linear or branched polyglyceryl ester, alkyl glyceryl ether or combinations thereof; and wherein the viscosity of the diluted anionic surfactant composition is less than 3,000 pascal seconds, at a shear rate of 0.25 s$^{-1}$ and at a temperature of 30° C., when diluted with an aqueous solvent.

The following examples illustrate the invention without limitation. All parts and percentages are given by weight unless otherwise indicated.

It will be understood that each of the elements described in the examples below, or two or more together may also find a useful application in other types of methods differing from the type described above. Without further analysis, the foregoing will so fully reveal the gist of the present disclosure that others can, by applying current knowledge, readily adapt it for various applications without omitting features that, from the standpoint of prior art, fairly constitute essential characteristics of the generic or specific aspects of this disclosure set forth in the appended claims.

The foregoing embodiments are presented by way of example only; the scope of the present disclosure is to be limited only by the following claims.

Example 1

The concentrations below are prepared from 70% SLES having 30% water mixed with a viscosity modifier to yield the concentrations for the compositions shown below; whereby the composition equals 100%.

TABLE 1

Surfactant compositions with varied viscosity modifiers

| Surfactant | % Conc. | Viscosity modifier | % conc. |
|---|---|---|---|
| SLES | 63% | phenoxyethanol | 10% |
| SLES | 66.5% | benzyl alcohol | 5% |
| SLES | 63% | ethylhexylglycerin | 10% |
| SLES | 63% | polyglyceryl-10 caprylate/caprate | 5%:5% |
| SLES | 63% | phenoxyethanol + polyglyceryl-10 caprylate/caprate | 5%:5% |
| SLES | 63% | phenoxyethanol + ethylhexylglycerin | 5%:5% |

SLES: sodium lauryl ether sulfate

Figure 1:
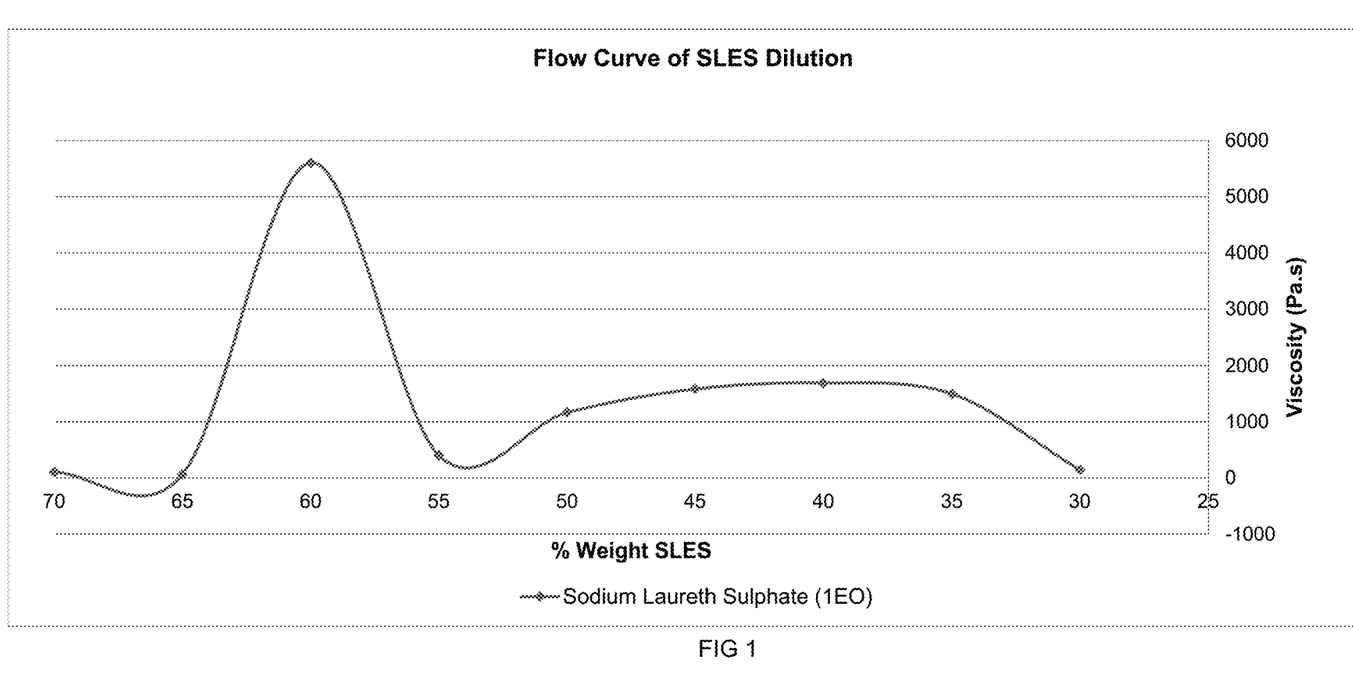
FIG. 1 Shows the viscosity range of SLES without any viscosity modifiers, using a cross-hatch Rheometer at 30° C. and 0.25 s$^{-1}$ shear rate.
Figure 2:
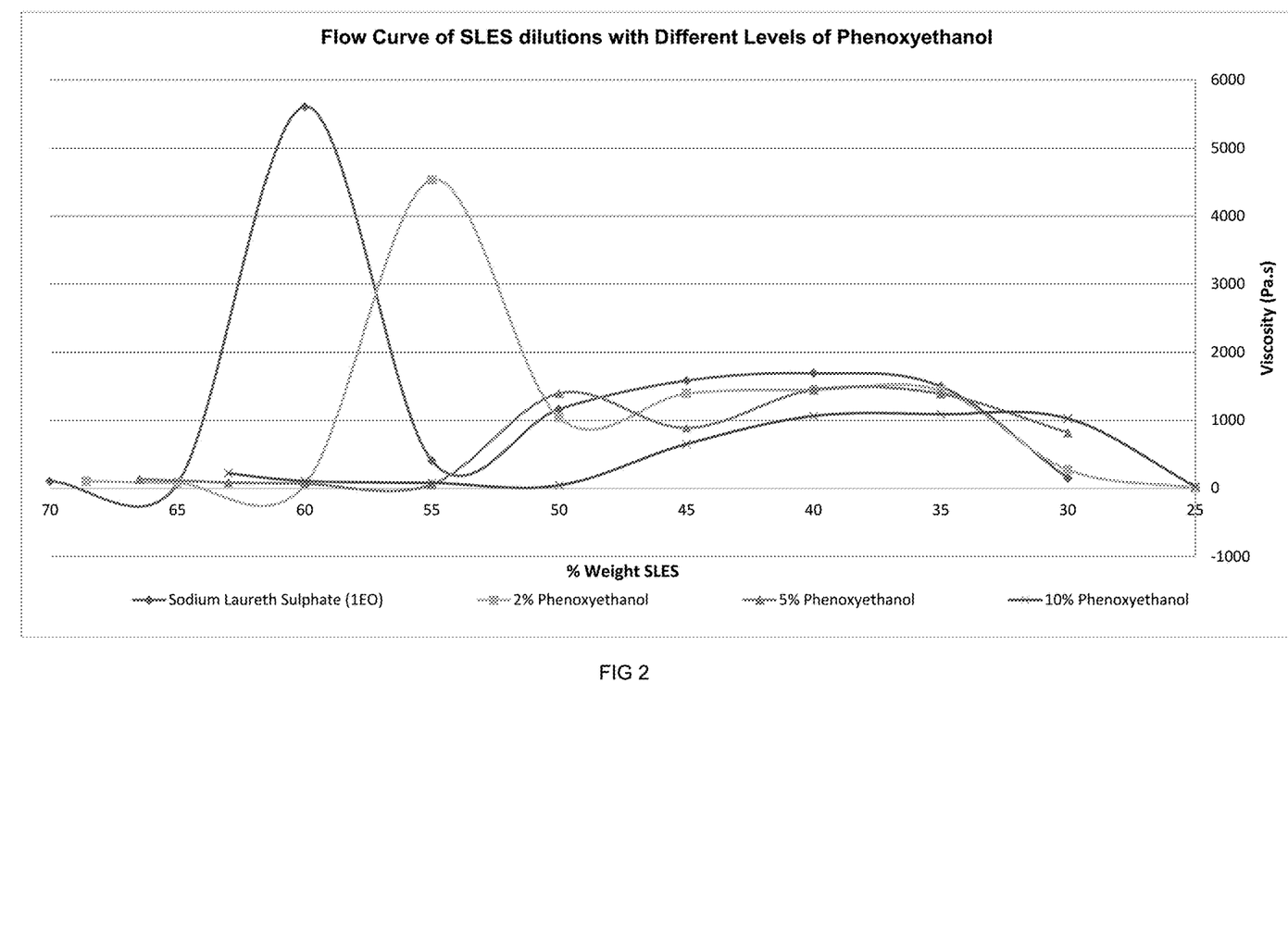
FIG. 2 Shows the viscosity range of SLES with viscosity modifier, phenoxyethanol having various concentrations, using a cross-hatch Rheometer at 30° C. and 0.25 s$^{-1}$ shear rate.

The addition of phenoxyethanol alone, as shown in FIG. 2, heavily suppressed the viscosity of SLES upon dilution, reducing the peak from 5607 Pa·s to 1090 Pa·s, at a shear rate of 0.25 s$^{-1}$ and at a temperature of 30° C., at 10% active. Multifunctional application of phenoxyethanol as a preservative also makes it the ideal component for final formulations. Results showed that increasing levels of phenoxyethanol in 70% active SLES greatly suppresses, not only the maximum viscosity of the viscoelastic cubic phase, but also seemingly delays the onset of the phase from 65% active down to as low as 30% active in the 10% phenoxyethanol. In one aspect, when considering total phenoxyethanol carry over into the final formulation, 5% phenoxyethanol appears to offer the best compromise in terms of performance verses regulatory constraints whilst still allowing the final formulation to salt thicken. These results show great promise for improving the processability of high activity SLES at large scale without the need for specialist equipment.

Figure 3:
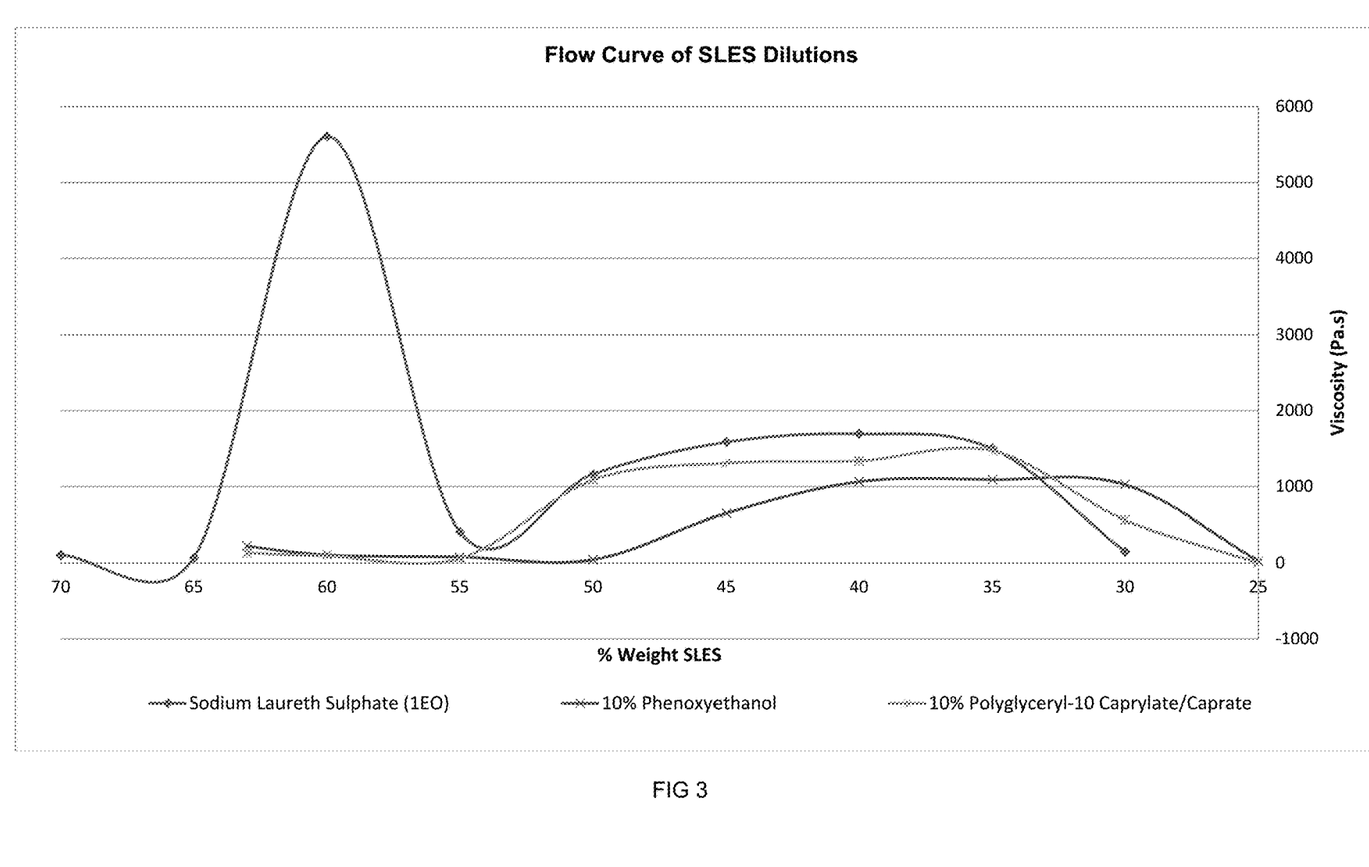
FIG. 3 Shows the viscosity range of SLES with viscosity modifier, polyglyceryl-10 caprylate/caprate in comparison to phenoxyethanol, using a cross-hatch Rheometer at 30° C. and 0.25 s$^{-1}$ shear rate.

As shown in FIG. 3, the comparison of 10% polyglyceryl-10-caprylate/caprate and 10% phenoxyethanol independently, as a viscosity modifier for SLES, upon dilution. Both actives showed similar viscosity values.

Figure 4:
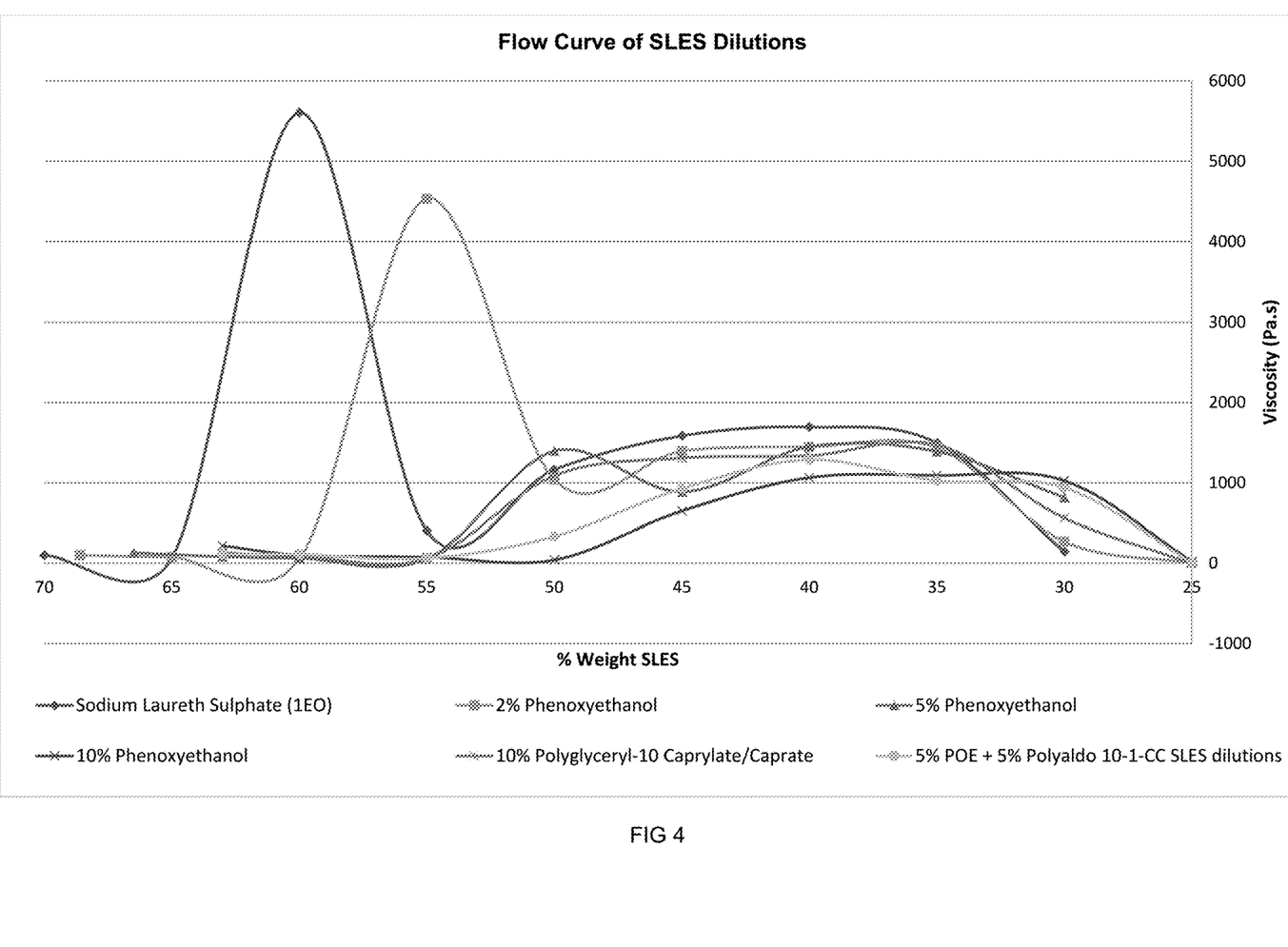
FIG. 4 Shows the viscosity range of SLES with a blend of viscosity modifiers, specifically a blend of 0.01%-10% phenoxyethanol and 0.01%-10% polyglyceryl-10 caprylate/caprate; in comparison to phenoxyethanol alone, using a cross-hatch Rheometer at 30° C. and 0.25 s$^{-1}$ shear rate.

As shown in FIG. 4, the addition of phenoxyethanol (POE) and polyglyceryl-10-caprylate/caprate combination in comparison to phenoxyethanol and polyglyceryl-10-caprylate/caprate alone. The combination showed to significantly altered the rheological behavior of SLES upon dilution. Results from the addition of phenoxyethanol and polyglyceryl-10-caprylate/caprate combination to SLES reduced the rheological behavior of SLES. The data shows that the onset of the viscoelastic range occurs at 50%-30% active SLES, which is comparable to 5% phenoxyethanol. The active viscosity drop, however, is better than 5% phenoxyethanol, but not quite as effective as 10% phenoxyethanol as shown in FIG. 2.

Figure 5:
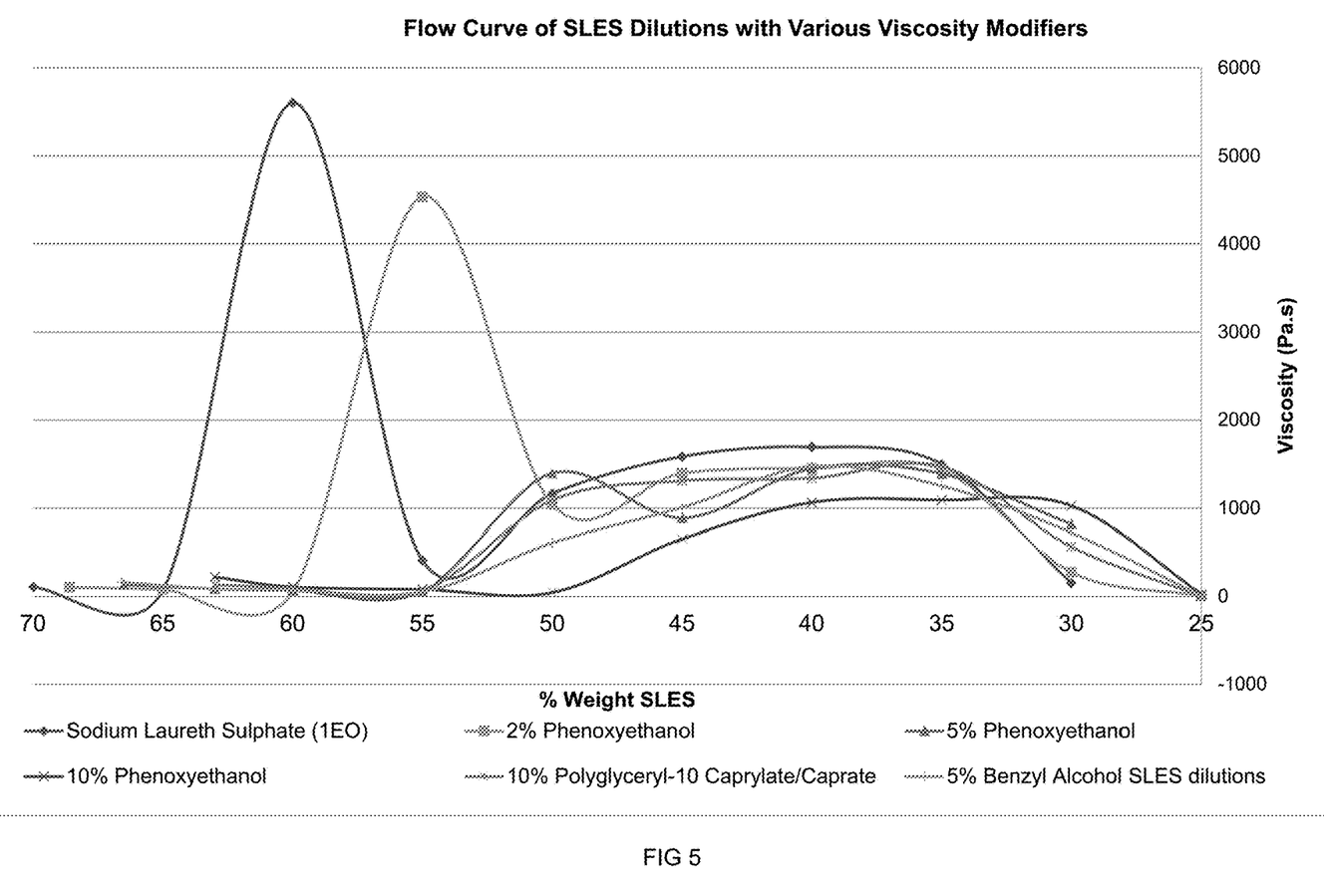
FIG. 5 Shows the viscosity range of SLES with various viscosity modifiers. Measured comparison of ethylhexylglycerin, phenoxyethanol and benzyl alcohol, using a cross-hatch Rheometer at 30° C. and 0.25 s−1 shear rate.

Benzyl alcohol is under the same regulatory restrictions as Phenoxyethanol hence the use of 5% rather than 10%. As shown in FIG. 5, 5% Benzyl alcohol was compared to 2%, 5%, and 10% phenoxyethanol and polyglyceryl-10-caprylate/caprate independently; showed slightly more favorable for benzyl alcohol. The data shows how benzyl alcohol appears to suppress the viscoelastic behavior of SLES greater than 5% phenoxyethanol does, particularly at lower shear rates, with results comparable to the blend of phenoxyethanol and polyglyceryl-10 caprylate/caprate.

Figure 6:
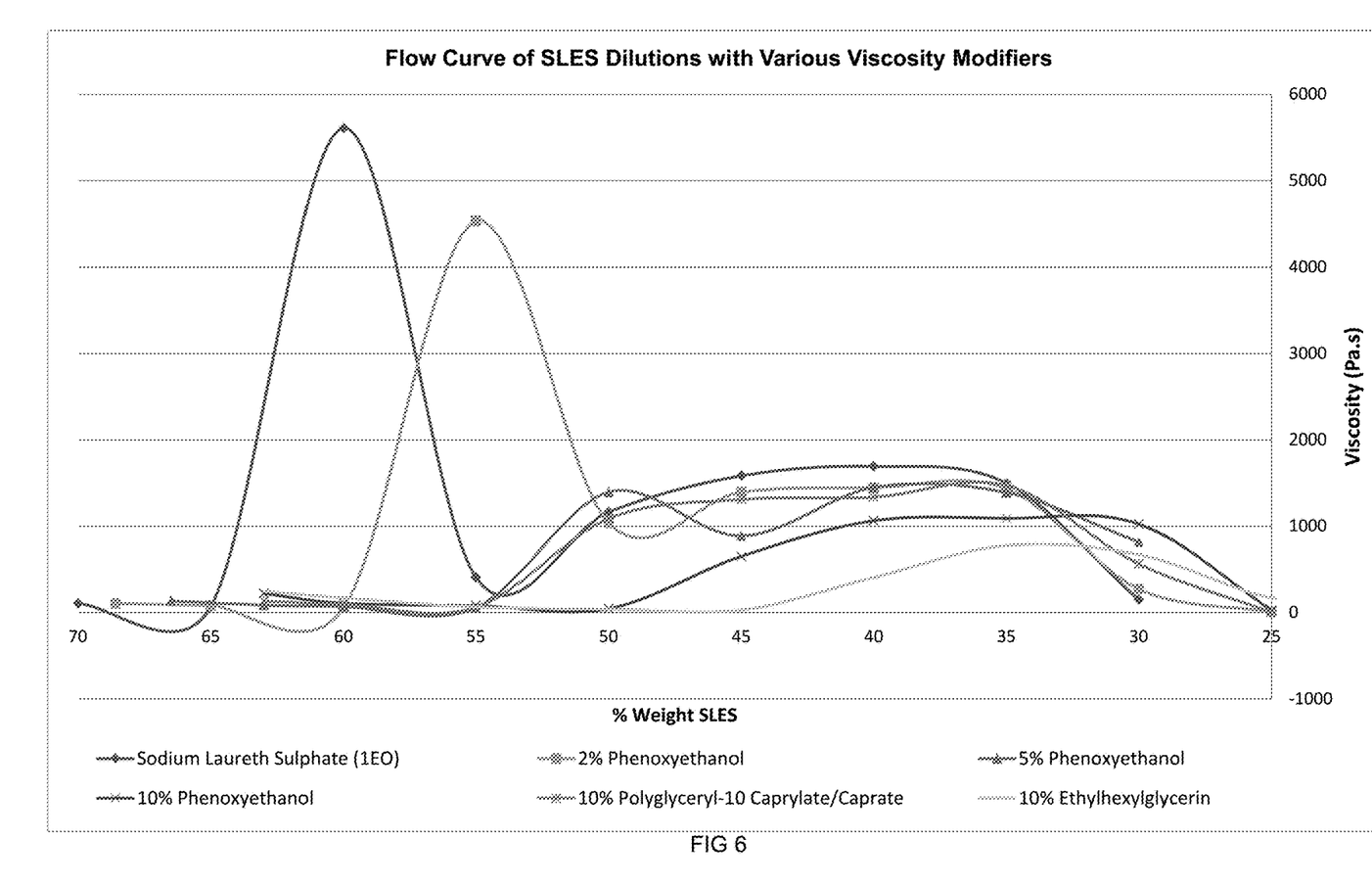
FIG. 6 Shows the viscosity range of SLES with various viscosity modifiers. Measured comparison of ethylhexylglycerin, phenoxyethanol and polyglyceryl 10 caprylate/caprate, using a cross-hatch Rheometer at 30° C. and 0.25 s$^{-1}$ shear rate.

The efficacy of viscosity modifier, ethylhexylglycerin, is shown in FIG. 6. Ethylhexylglcyerin (EHG) showed to be the most effective active at suppressing the viscosity of SLES upon dilution, to a peak of 776 Pa·s; resulting in an 86% reduction of the cubic phase; in comparison to the use of phenoxyethanol or polyglyceryl-10-caprylate/caprate.

Figure 7:
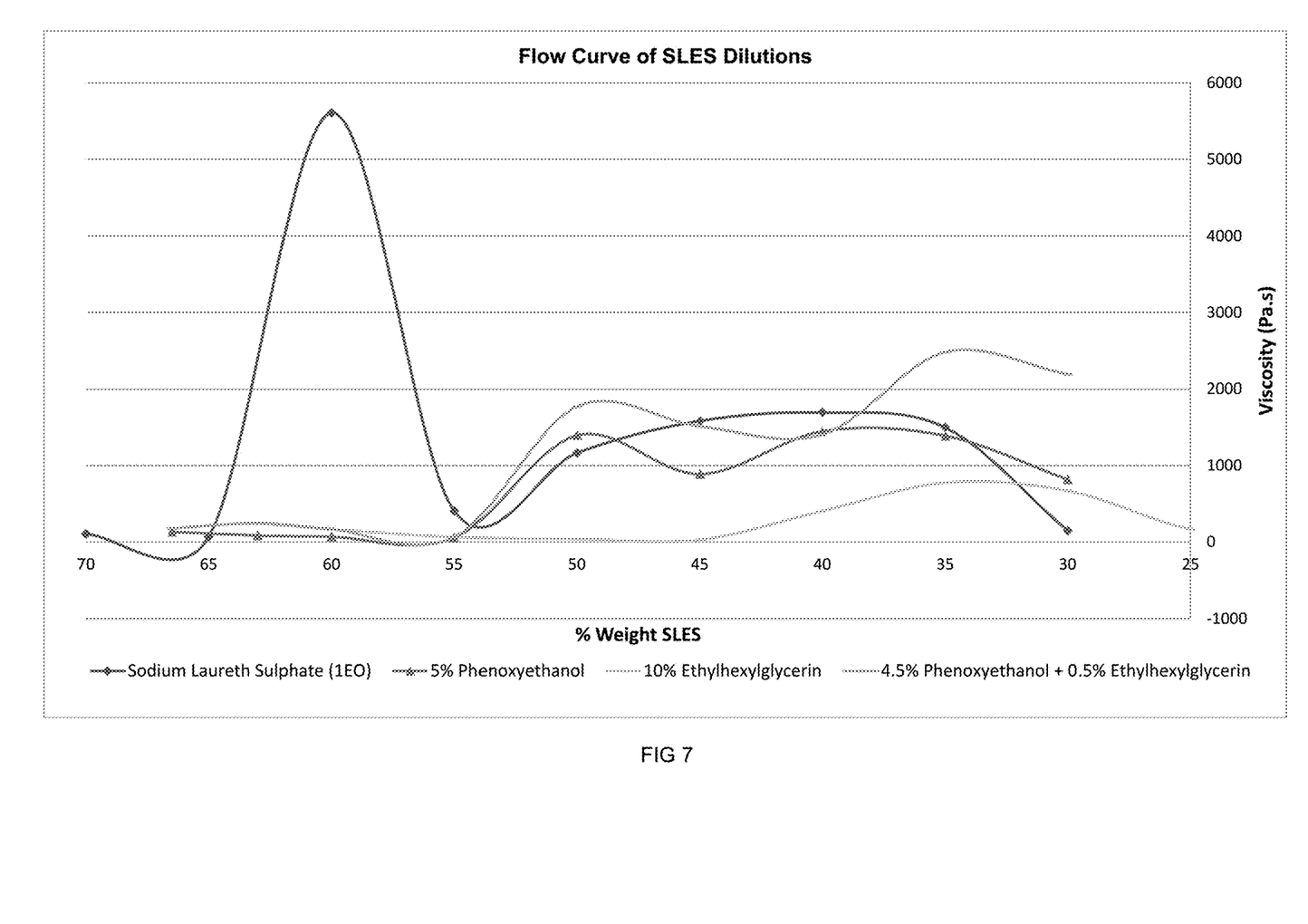
FIG. 7 Shows the viscosity range of SLES with viscosity modifiers, specifically 0.01%-10% phenoxyethanol, 0.01%-10% ethylhexylglycerin and a blend thereof, using a cross-hatch Rheometer at 30° C. and 0.25 s$^{-1}$ shear rate.

Additionally, the blend of phenoxyethanol and ethylhexylglycerin is shown in FIG. 7, in comparison to 5% phenoxyethanol alone. Results showed to also very effective at high % weight levels; however, at lower dilutions level the blend seems to have an antagonistic effect and actually builds the viscosity.

Figure 8:
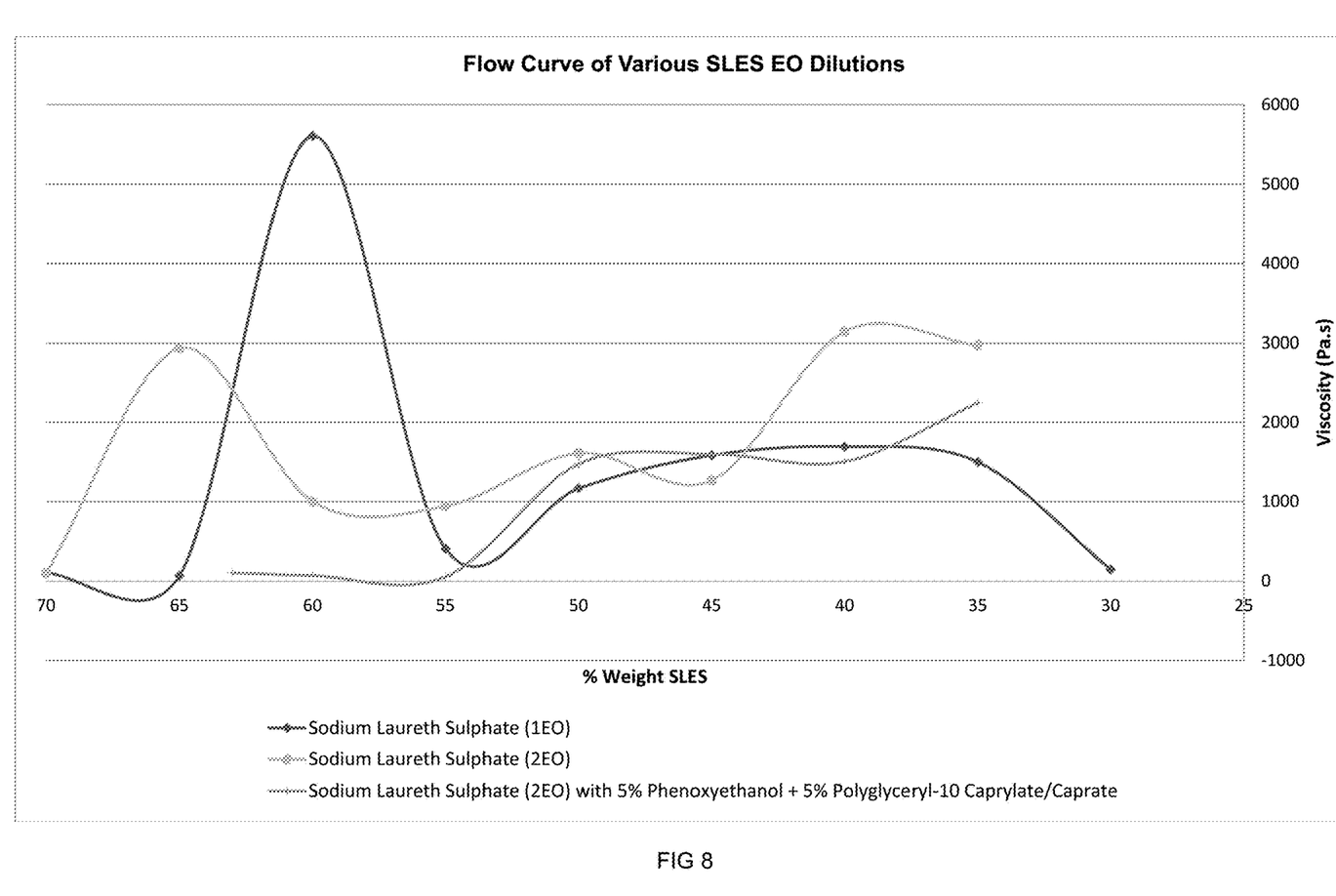
FIG. 8 Shows the viscosity range of shows the comparison between mole ratio of 1:−3. Specifically, the comparison of 1:2 EO SLES; 1:1 EO SLES and 2 EO SLES with a viscosity modifier blend, using a cross-hatch Rheometer at 30° C. and 0.25 s$^{-1}$ shear rate.

The molar range of ethylene oxide to a $C_8$-$C_{32}$ alcohol; typically varies from 0.5-10; suitably from 1-5; desirably from 1-3. FIG. 8 highlights the differences between ethylene oxide (EO) levels were n=1, 2 and 3. It shows how increased ethoxylation significantly reduces the viscoelastic phase behavior of the $R^1$ group in Formula I. The transition from lamellar to cubic phase for an ethoxylated $C_8$-$C_{32}$ alcohol when n=1 can be easily observed between 60 w/w % to 65% w/w with a sudden viscosity jump from 67 Pa·s to 5600 Pa·s.; by comparison when n=3 the cubic phase transition is not easily visible.

When measuring viscosity using a rheometer it is important to note the shear rate, plate type, gap, even the model of machine can give drastically different readings. Readings are best used as relative measurements rather than absolute.

Figure 9:
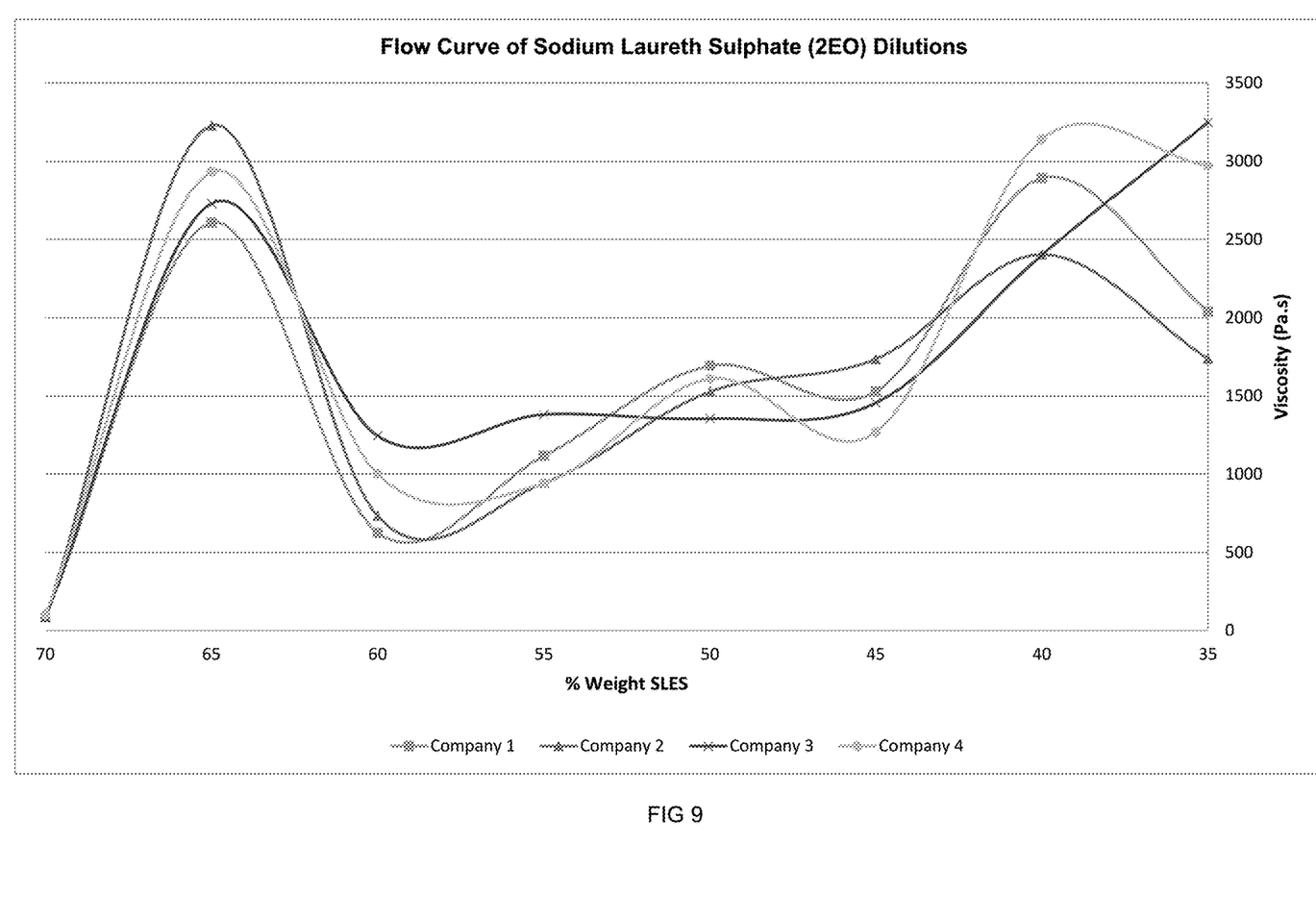
FIG. 9 Shows the manufacturing/Processing variations from different companies can cause differences to the cubic phase profile. Four different ethylene oxide (EO) grades from Company 1, Company 2, Company 3, and Company 4. Results showed that the 2EO grades are remarkably consistent suggesting any additives that suppress the cubic phase would be universal and not require customization per grade.

Furthermore, the data appeared ideal and remarkably consistent despite the source of the $C_8$-$C_{32}$ ethylene oxide (EO), as shown in FIG. 9; suggesting that all sources of ethylene oxide functioned identically in suppressing the cubic phase, illustrating universal results without the need to customize per grade of the active.

While the invention has been described above with references to specific embodiments thereof, it is apparent that many changes, modifications and variations can be made without departing from the invention concept disclosed herein. Accordingly, it is intended to embrace all such changes, modifications, and variations that fall within the spirit and broad scope of the appended claims.

What is claimed is:

1. A flowable liquid anionic surfactant concentrate comprising:
   (a) an anionic surfactant solution comprising 30 w/w % to 90 w/w % by weight of an alkyl ether sulfate, having a Formula (I):

$$R^1O(CH_2CH_2O)_nSO^3X \qquad (I)$$

wherein $R^1$ is a $C_8$-$C_{32}$ linear or branched, substituted or unsubstituted alkyl,
   n is a number having a value from 1-10,
   X is an alkali metal, alkaline earth metal, ammonium, alkylammonium, alkanolammonium or glucammonium;
   (b) 0.01 w/w % to 20 w/w % of a viscosity modifier comprising an aromatic alcohol, wherein the aromatic alcohol comprises benzyl alcohol or derivatives thereof, phenoxyethanol or derivatives thereof, or mixtures thereof, a $C_6$-$C_{22}$ linear or branched polyglyceryl ester wherein the $C_6$-$C_{22}$ linear or branched polyglyceryl ester comprises polyglyceryl-10 caprylate/caprate, or combinations thereof; and
   (c an aqueous solvent in an amount sufficient for a total equaling 100%, wherein the aqueous solvent is free of salt solutions;
   wherein upon dilution with an aqueous solvent, the concentrate remains flowable.

2. The flowable liquid anionic surfactant concentrate, according to claim 1, wherein the aqueous solvent is water.

3. The flowable liquid anionic surfactant concentrate, according to claim 1, wherein n is a value from 0.5 to 5.

4. The flowable liquid anionic surfactant concentrate, according to claim 1, wherein X is an alkali metal comprising sodium or potassium; an alkaline earth metals comprising magnesium or calcium; alkylammonium, alkanolammonium or glucammonium.

5. The flowable liquid anionic surfactant concentrate, according to claim 1, wherein $R^1$ comprises a caprylic, capric, lauryl, isotridecyl, myristyl, cetyl, stearyl, oleyl, isostearyl, arachidyl, behenyl or mixtures thereof.

6. The flowable liquid anionic surfactant concentrate, according to claim 1, wherein the alkyl ether sulfate comprises sodium lauryl ether sulfate, ammonium lauryl ether sulfate or mixtures thereof.

7. The flowable liquid anionic surfactant concentrate, according to claim 1, further comprising ethylhexylglycerin.

8. The flowable liquid anionic surfactant concentrate, according to claim 1, wherein the concentrate comprises 40 w/w % to 80 w/w % active of an alkyl ether sulfate.

9. The flowable liquid anionic surfactant concentrate, according to claim 1, wherein the diluted concentrate has a viscosity value less than 3,000 pascal seconds, at a shear rate of 0.25 s$^{-1}$ and at a temperature of 30° C., when diluted in an aqueous solvent.

10. The flowable liquid anionic surfactant concentrate, according to claim 1, comprising (a) 45 w/w % to 75 w/w % of an alkyl ether sulfate comprising sodium lauryl ether sulfate, ammonium lauryl ether sulfate or combinations thereof; and (b) 0.01 w/w % to 20 w/w % of aromatic alcohol wherein the aromatic alcohol is phenoxyethanol or derivatives thereof, benzyl alcohol or derivatives thereof, 4-(2-Hydroxyethyl)phenol, or combinations thereof.

11. The flowable liquid anionic surfactant concentrate, according to claim 1, comprising (a) 45 w/w % to 75 w/w % of an alkyl ether sulfate comprising sodium lauryl ether sulfate, ammonium lauryl ether sulfate or combinations thereof; and (b) 0.01 w/w % to 20 w/w % of the $C_6$-$C_{22}$ linear or branched polyglyceryl ester; wherein the ester comprises polyglyceryl-10 caprylate/caprate.

12. The flowable liquid anionic surfactant concentrate according to claim 1, comprising (a) 45 w/w % to 75 w/w % of an alkyl ether sulfate comprising sodium lauryl ether sulfate, ammonium lauryl ether sulfate or combinations thereof; and (b) 0.01 w/w % to 10 w/w % of phenoxyethanol and 0.01 w/w % to 10 w/w % polyglyceryl-10 caprylate/caprate.

13. The flowable liquid anionic surfactant concentrate according to claim 1, comprising (a) 45 w/w % to 75 w/w % of an alkyl ether sulfate comprising sodium lauryl ether sulfate, ammonium lauryl ether sulfate or combinations thereof; and (b) 0.01 w/w % to 10 w/w % of phenoxyethanol and further comprising 0.01 w/w % to 10 w/w % ethylhexylglycerin.

14. A personal care composition comprising from 0.01 w/w % to 50 w/w %, of the flowable liquid anionic surfactant concentrate according to claim 1, based on the total weight of the personal care composition.

15. A method of reducing the viscosity increase of a liquid anionic surfactant concentrate during dilution with water, the method comprising:
(i) providing 30 w/w % to 90 w/w % of an anionic surfactant which exhibits a viscosity increase during dilution with an aqueous solvent comprising
an alkyl ether sulfate, having a Formula (I):

$$R^1O(CH_2CH_2O)_nSO^3X \qquad (I)$$

wherein $R^1$ is a $C_8$-$C_{32}$ linear or branched, substituted or unsubstituted alkyl, n is a number having a value from 0.5-10;
X is an alkali metal, alkaline earth metal, ammonium, alkylammonium, alkanolammonium or glucammonium,
(ii) adding 0.01 w/w % to 20 w/w % a viscosity modifier into the anionic surfactant the viscosity modifier comprising an aromatic alcohol, wherein the aromatic alcohol comprises benzyl alcohol or derivatives thereof, phenoxyethanol or derivatives thereof, or mixtures thereof a $C_6$-$C_{22}$ linear or branched polyglyceryl ester, wherein the $C_6$-$C_{22}$ linear or branched polyglyceryl ester comprises polyglyceryl-10 caprylate/caprate, or combinations thereof; and
(iii) mixing the viscosity modifier, the anionic surfactant and an aqueous solvent in an amount sufficient for a total equaling 100% together, wherein the aqueous solvent is free of salt solutions.

16. The method according to claim 15, wherein the alkyl ether sulfate, having a Formula (I) comprises sodium lauryl ether sulfate, ammonium lauryl ether sulfate or combinations thereof.

17. The method according to claim 15, wherein the viscosity modifier comprises a blend of two or more viscosity modifiers having varied ratios ranging from about 1-100 to 100-1.

18. The method according to claim 15, wherein the aromatic alcohol comprises benzyl alcohol, phenoxyethanol, 4-(2-Hydroxyethyl)phenol, or combinations thereof.

19. The method according to claim 15, wherein the $C_6$-$C_{22}$ linear or branched polyglyceryl ester comprises polyglyceryl-10 caprylate/caprate.

20. The method according to claim 15, further comprising ethylhexylglycerin.

21. The method according to claim 15, wherein the aqueous solvent comprises water.

22. The method according to claim 15, wherein upon dilution with an aqueous solvent, having a viscosity value of less than 3,000 pascal seconds, at a shear rate of $0.25\ s^{-1}$ and at a temperature of 30° C.

23. The method according to claim 15, wherein the viscosity of the concentrate is less than 3000 pascal seconds, at a shear rate of $0.25\ s^{-1}$ and at a temperature of 30° C., when diluted with water.

* * * * *